United States Patent [19]

Groves et al.

[11] Patent Number: 4,535,284

[45] Date of Patent: Aug. 13, 1985

[54] HIGH AND LOW FREQUENCY ANALYSIS OF OSMOTIC STRESS OF CELLS

[75] Inventors: Michael R. Groves; Carlos M. Rodriguez, both of Miami, Fla.

[73] Assignee: Coulter Electronics, Inc., Hialeah, Fla.

[21] Appl. No.: 282,293

[22] Filed: Jul. 10, 1981

[51] Int. Cl.³ .......................................... G01N 27/00
[52] U.S. Cl. .................................................. 324/71.1
[58] Field of Search ........................... 324/71.1, 71.4; 364/555

[56] References Cited

U.S. PATENT DOCUMENTS

| | | | |
|---|---|---|---|
| 2,656,508 | 10/1953 | Coulter | 324/71.1 |
| 3,259,842 | 7/1966 | Coulter et al. | 324/71.1 |
| 3,502,973 | 3/1970 | Coulter et al. | 324/71.1 |
| 3,502,974 | 3/1970 | Coulter et al. | 324/71.1 |
| 3,603,875 | 9/1971 | Coulter et al. | 324/71.1 |
| 3,836,849 | 9/1974 | Coulter et al. | 324/71.1 |
| 4,278,936 | 7/1981 | Shine | 324/71.1 |
| 4,374,644 | 2/1983 | Armstrong | 324/71.4 |

OTHER PUBLICATIONS

"High Resolution Particle Analysis—Its Application to Platelet Counting and Suggestions for Further Application in Blood Cell Analysis", John L. Haynes, *Blood Cells,* 6, 201-213, 1980.

"Erythrocyte Osmotic Fragility: Micromethod Based on Resistive-Particle Counting", Adrian R. L. Gear, *J. Lab. Clin. Med.,* pp. 914-928, Nov., 1977.

*Primary Examiner*—Michael J. Tokar
*Assistant Examiner*—Kevin D. O'Shea
*Attorney, Agent, or Firm*—Gerald R. Hibnick; William A. Newton

[57] ABSTRACT

Disclosed is a method wherein osmotic activity of biological cells immersed in a suspension solution is induced by an osmotic or lytic shock and is monitored in an electronic volume sensing particle analyzer of the Coulter Counter ® type, the method including the steps of passing a high frequency current and a low frequency current through an aperture of said particle analyzer to create detectable signals for classifying the cells into populations of unaltered, altered, and ghost cells.

19 Claims, 8 Drawing Figures

HIGH AND LOW FREQUENCY ANALYSIS OF OSMOTIC STRESS OF CELLS

FIELD OF THE INVENTION

The invention pertains to a method in which the electrical resistance measurements for biological cells, such as red blood cells, are changed by the immersion of the cells in a volume changing agent. This change in electrical resistance generates a set of related data, which defines a pattern which is characteristic of the health or physiological condition of the human or animal source of the cell sample.

BACKGROUND OF THE INVENTION

The study of human cells for medical screening, diagnostic and other medical purposes is well known. For example, red blood cell count, mean cell volume (MCV), hemoglobin content and hematocrit are well known and commonly employed red blood cell parameters used in medical study and patient care.

The red blood cell is an excellent osometer in that the cell will change in shape and volume, depending on the osmotic pressure or chemical nature of the fluid surrounding it. If the red blood cell is suspended in a solution of the same osmotic pressure as that of the intracellular fluid, the suspending fluid is said to be isotonic. Should the red blood cell be suspended in a hypotonic suspending solution, the red blood cell will swell and may even rupture, due to the intake of water, in an effort to balance the internal osmotic pressure to that of the suspending solution. Other cells of the blood, namely the white blood cells and platelets, will act in much the same manner.

It is also well known that the osmotic pressure of solutions, i.e., their osmolality, such as saline solutions, varies with their concentration and types of solutes, in that the difference between the osmotic pressure within a cell and that of its suspension liquid causes the previously described change in volume and also a change in electrical resistance. In addition to a hypotonic solution, other volume changing solutions are known in the art. For instance, when red blood cells are exposed to hemolytic agents such as saponin, their membrane lipids are altered, so that water is allowed to enter the cell, causing the cell to swell and eventually rupture. If an excess of lytic agent is used, the red cell may be completely ruptured into extremely small fragments.

Cell and particle counting and measuring instruments, examples being those sold under the trademark Coulter Counter ® by Coulter Electronics, Inc., Hialeah, Fla., employ electronic sensing means which directly respond to the electrical resistance of each cell to count and measure each cell and progressively record cell parameters of a sample of cells in an isotonic solution. The Coulter Counter ® particle measuring instruments operate upon the well-known and documented principle of particle and cell measurement employing a sensing aperture path, which also is disclosed in Coulter U.S. Pat. No. 2,656,508 and improvement U.S. Pat. No. 3,259,842. The response of a Coulter Counter ® electric sensor is influenced at least by the shape, deformability and flow rate of the microscopic item being measured as it flows through the sensing aperture path. Since cells are subject to some deformation as they pass through the sensing aperture path, their electrical resistance measurement and their measured volume may differ from their true volume. To distinguish between true volume and measured volume, the term "apparent volume" will be employed herein to refer to measured volume. It is also well-known that as the cells swell and their pores expand, the cell will be more conductive of the current so that its apparent volume will decrease with respect to its true volume.

In the commercial Coulter Counter ® particle analyzer constructed in accordance with the heretofore mentioned U.S. Pat. No. 2,656,508, field excitation has been supplied by a direct current or low frequency source. As previously described, the electrical change caused by the passage of a particle through the electric field of small dimensions, excited by a direct or low frequency current, is approximately proportional to particle size. A direct current is considered to be of zero frequency in this application. However, the impedance sensing principle has been materially expanded to provide information concerning particles being studied, not limited only to characteristics due to the size of particles, but including characteristics due to the composition and nature of the material constituting the particles, as disclosed in U.S. Pat. No. 3,502,974 to Coulter et al and U.S. Pat. No. 3,502,973 to Coulter et al. These prior art apparatuses generally have at least two current sources, both of which are applied to the sensing zone simultaneously, one having a radio frequency and the other being a "zero frequency" direct current or, alternatively, having a sufficiently low frequency that the reactive part of the particle impedance has a negligible effect on the response of the apparatus. At radio frequencies, the high frequency current shunts the cell's membrane so that the high frequency measurement gives a size measurement which is function of the cell's size and its internal conductance. One of the useful particle descriptors that can be obtained from this dual source arrangement is known in the art as the "opacity" of the particles. With a biological cell, opacity measures the internal conductivity of the cell. Opacity also can be described as measuring the ratio of size as measured at radio frequency to size as measured at low or zero frequency.

U.S. Pat. No. 3,836,849 to Coulter et al teaches that cells can be treated, for example, by a lysing agent to selectively cause the electronically measured opacity of different types of cells to change; whereby, each distinctive type of cell acquires a distinctive opacity range that is subject to electronic detection.

In U.S. patent application Ser. No. 118,727 to Shine, filed Feb. 5, 1980 and now U.S. Pat. No. 4,278,936 a method is described wherein biological cells are subjected to hypotonic solutions having different osmolalities. This causes the cells to rapidly attain a change in volume and electrical resistance parameters, which change is measurable by the above described Coulter Counter ® particle analyzer.

In U.S. patent application Ser. No. 251,668, filed April 6, 1981, to Armstrong, now U.S. Pat. No. 4,374,644 there is disclosed a method wherein cells are subjected to a hypotonic solution or a solution having a lytic agent, causing the cells to attain a change in volume and electrical resistance parameters. This change is measured as a function of time by a Coulter Counter ® particle analyzer.

In the article entitled "Erythrocyte Osmotic Fragility: Micromethod based on Resistive-particle Counting", by Adrian Gear, J. Lab. Clin. Med., Vol. 90, No. 5, pp. 914 (1977), there is described a method wherein cells in a hypotonic solution are subjected to higher than normal D.C. currents to obtain two—distinct peaks for intact and ruptured cells.

In the article entitled "High-Resolution Particle Analysis—Its Application to Platelet Counting and Suggestions for Further Application In Blood Cell Analysis", by John Hanes, Blood Cells 6, p. 201-213 (1980), there is described a method wherein numerous hypotonic solutions are prepared with cells therein and then the cells are put into a normal saline solution. When the MCV of the cells is then measured using a DC current in an electronic volume sensing particle analyzer, it is claimed that two distinct peaks are obtained for the intact and the ruptured cells. From this data the ratio or percent lysis is calculated at each ionic strength.

U.S. Pat. No. 4,278,936 to Shine and U.S. Pat. Nos. 3,502,973 and 3,502,974 to Coulter et al are incorporated by reference herein.

SUMMARY OF THE INVENTION

The present invention is directed toward a method wherein osmotic activity of biological cells immersed in a suspension solution is induced by an osmotic or lytic shock and is monitored in a particle analyzer of the Coulter Counter ® type having an aperture for electronic particle volume sensing. The improvement of the invention comprises passing a high frequency current through said aperture to generate a detectable high frequency signal for each cell passing therethrough. By monitoring these high frequency signals, the cells can be classified into the subpopulations of unaltered and altered cells with a relatively high degree of signal resolution. The relative numbers of cells in these subpopulations can be determined at one or more states of the osmotic activity so as to provide means for discriminating between normal and abnormal blood samples.

In addition to the high frequency current signal, a low frequency current can be simultaneously passed through the aperture to generate a detectable low frequency signal for each cell passing therethrough. The low and high frequency signals can be monitored and detected to give correlated low and high frequency measurements for each cell. In one application of the low frequency signal, the high frequency measurement can be divided by the low frequency measurement to give an opacity measurement. From this opacity measurement, the above described two subpopulations can be obtained. In a second application of the low frequency signal, a two dimensional matrix of the low frequency measurement and the high frequency measurement or, alternatively opacity, can be used to obtain the three subpopulations of unaltered, altered and ghost cells. In other words, a third subpopulation, ghost cells, can be obtained with a relatively high degree of resolution.

BRIEF DESCRIPTION OF THE DRAWINGS

Further objects and advantages of the present invention will become apparent as the following description proceeds, taken in conjunction with the accompanying drawing in which:

FIGS. 3A through 3D show plots of particle data points for blood samples, in which: FIG. 3A is for a normal blood sample in 330 milliosmols saline;

FIG. 3B shows an abnormal blood, Beta thalassemia, in a saline solution with an osmolality of 330 milliosmols;

FIG. 3C shows a normal blood sample in a saline solution having an osmolality of 109 milliosmols;

FIG. 3D shows an abnormal blood, Beta thalassemia, in a saline solution having an osmolality of 109 milliosmols.

DETAILED DESCRIPTION OF PREFERRED EMBODIMENTS

Figure 1:
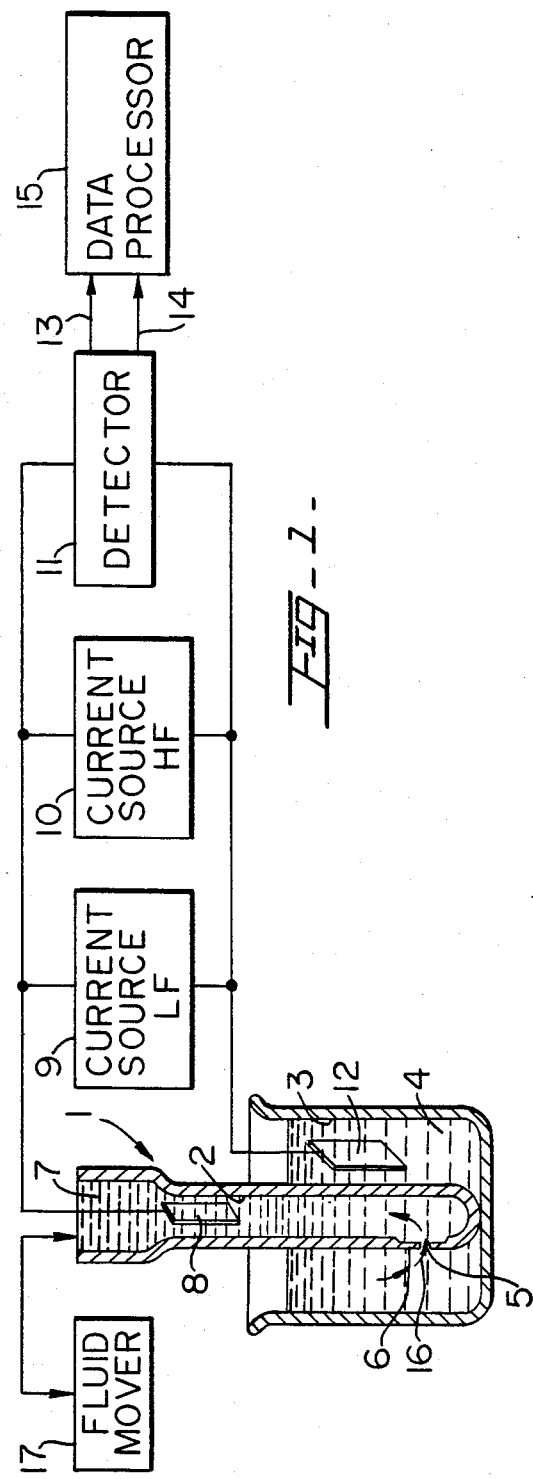
FIG. 1 shows a generalized flow cytometer for use with the first example of the present invention.

In FIG. 1, there is shown a type of particle analyzing apparatus 1 in which the method embodying the invention is employed. The apparatus 1 which comprises a first vessel 2 and a second vessel 3 for holding a body of fluid 4 having particles suspended therein. The end of the first vessel 2 has a microscopic aperture 5 formed in an insulating wafer 6. A body of fluid 7 is in the interior of the vessel 2 and an electrode 8 is suspended therein and is connected to a pair of current sources 9 and 10, and to a detector 11. A common electrode 12 is suspended in the body of fluid 4 and is connected to the current sources 9 and 10 and the detector 11. The detector 11 possesses two parallel electronic channels having terminating lines 13 and 14 for connection to inputs of a data processor 15. Depending upon the application, the data processor 15 can include a computer with memory and calculating means and a plotter.

The fluid 4 and particles are caused to move through the aperture 5, as indicated by the broken line path 16, by reason of a fluid mover structure 17 that is connected with the first vessel 2. The fluid mover structure 17 can conveniently comprise a manometer syphon arrangement. For most purposes, the fluids 4 and 7 can be the same and comprise an electrolyte having an impedance different from that of the suspended particles. The apparatus, as described so far, is illustrated in its simplist, well known form. Depending on the specific application of the method embodying the invention, the apparatus may take more complex, known designs.

The current source 9 can be a direct current source and the other current source 10 can be a radio frequency (r.f.) source. In combination, they define a sensing field which lies in and closely adjacent the aperture 5. Each time that a particle passes through the sensing field, there will be a change in the impedance of the sensing field and there will be a component of the change which will be attributable to each frequency. These components are separated in the detector 11 and electrical pulses, which have their respective amplitudes dependent upon the changes caused by the particle at the particular frequency, are produced so as to appear on the channel terminals 13 and 14. Reference to direct current of the current source 9 is not intended to exclude low frequency; likewise, r.f. frequencies of the current source 10 encompass frequencies high with respect to the low frequency of the current source 9. The signal produced by the current source 9 will be labeled as a "low frequency (LF) size signal", which is produced at terminal 13, and the signal produced by the current source 10 will be labeled as a "high frequency (HF) size signal", which is produced at terminal 14. When the HF signal is divided by the LF signal, an opacity signal, i.e., HF/LF signal, is obtained, such signal correlating with the internal conductivity of the cell.

The apparatus and its components described above are those of a known type of particle analyzer disclosed in U.S. Pat. Nos. 3,502,973 and 3,502,974, both of which have been incorporated herein. Only those components of the particle analyzing apparatus 1 have been shown which are necessary to the explanation of the implementation of the method incorporating the present invention.

The method embodying the invention comprises initially giving biological cells, such as red blood cells, an initial osmotic or lytic shock by one of many different, well known techniques that are described in the following examples. After an individual cell experiences an initial osmotic or lytic shock, its electrical characteristics, as measured by the particle analyzer apparatus 1, will normally be changed, which allows the cells to be divided into two or three subpopulations with reasonably good resolution. The cells that display substantially unaltered LF and HF size signals, and therefore unaltered opacity signals, are termed the "unaltered" cells. Those cells that display an altered HF size signal and/or opacity signal are termed "altered" cells. These altered cells will have a smaller HF size signal. The LF signal will depend upon the particular experimental conditions employed; however, typically the LF signal will remain the same or be slightly increased. Finally, those cells that display a very small, negligible or non-detectable HF size signal and opacity signal are termed "ghosts". The term "intact" cells will be used to refer to altered and unaltered cells grouped together. At least a portion of HF signals are so negligible as not to be detectable by the detector 11, but by obtaining a LF signal for a given cell, it is possible to recognize the fact that a non-detectable, negligible HF signal exists for that cell. This allows the cell to be classified as a ghost cell, along with those cells that give detectable HF signals substantially lower than the altered cells. Hence, by utilizing these signals, the number of cells that fall within each of the above classes or subpopulations can be determined. This allows for the osmotic activity of the cells to be quantified, i.e., by specifying the number of cells in each subpopulation. Moreover, meaningful data is obtained by comparing the number of cells in any two subpopulations. Also, in some of the techniques described hereinafter, osmotic activity is not carried out to a sufficient degree for the third population, ghost cells, to appear. The osmotic activity being monitored can take many different forms, as will be shown in the following examples.

EXAMPLE I

As implemented with the apparatus 1 of FIG. 1, a sample is prepared in the first vessel 2 by taking a known quantity of cells and adding to it a known quantity of diluent (described also as "suspension solution") in the form of a saline solution. At time zero, a quantity of a lytic agent, such as saponin, is added to the sample and the sample is introduced to the aperture 5 of the apparatus 1. The LF and HF signals are detected by the detector 11 and are stored in the data processor 15, along with a calculated opacity signal. After a given period of time, the experiment is stopped and the stored signal data is analyzed in the following way. From this data it can then be determined how many cells have remained unaltered, how many are altered, and how many have become ghosts, at any given time after the introduction of the lytic agent. Consequently, one can follow the kinetics of lysis (i.e., unaltered cells changing to altered or ghost cells) and extract, for example, the time at which 50% lysis occurs and the rate of lysis at this particular time. Because the LF signal is also monitored, the maximum attained sizes of intact (i.e., unaltered or altered) cells can also be obtained. These sizes, when compared with the initial sizes of the cells, give some measure of the increase in sizes that occurs during the lytic process. Since it is known that the maximum sizes of red blood cells occur when the cells are fully sphered and that their surface area remains constant, a calculation of the initial shape of the cell can then be made, when the sample includes red blood cells. It is possible to separate those cells that are still intact from those that are ghosts by looking at the opacity which approaches zero for the ghost cells. Hence, three subpopulations can be developed if lysis is allowed to proceed for a sufficient time.

EXAMPLE II

A sample of cells is continually mixed with a diluent in the form of a saline solution and subsequently introduced into the aperture of a Coulter Counter ® particle analyzer. This analyzer would be the same as shown in FIG. 1, except additional means are needed for varying the osmolality of the diluent or suspension liquid as a function of time, during the course of the experiment. Otherwise, the energizing, detection and data processing system is the same as that shown in FIG. 1. Such a particle analyzer is illustrated in the incorporated U.S. Pat. No. 4,278,936. More specifically, the apparatus required for Example II is the same as that shown in FIG. 2, when the components marked by a dashed box 18 are removed and a non-hydrodynamically focused aperture is used. The apparatus of FIG. 2 will be described hereinafter.

At time zero the osmolality may be, for example, that of normal physiological saline, i.e., 0.9% NaCl, while at any later time the osmolality has dropped, ultimately to the level at which osmotic lysis of the cells occurs. In this particular example, a non-hydrodynamically focused aperture 5 is used, such as shown in FIG. 1 and in said incorporated U.S. Pat. No. 4,278,936. The LF, HF and opacity signals are obtained for the individual cells and stored as a function of the osmolality of the medium in which the particular cells were suspended. The data is subsequently analyzed to yield, for example, the osmolality at which the 50% of the cells have become ghost cells, the rate of formation of ghost cells given the change in osmolality at this particular osmolality point, and the maximum increase in size of the intact cells. It is possible to separate those cells that are still intact from those that are ghosts, if any, by looking at the opacity which approaches zero for the ghost cells. Consequently, when looking at the size of the swollen cells, the ghost cells, if any, can be removed from consideration. As in Example I, this information provides knowledge of the initial shape of the cells, if red cells are used in this experiment. If length of time of immersion before sensing is sufficiently short and the osmolality of the solution is sufficiently high, there will not be any ghost cells for at least the upper range of osmolalities.

EXAMPLE III

Figure 5:
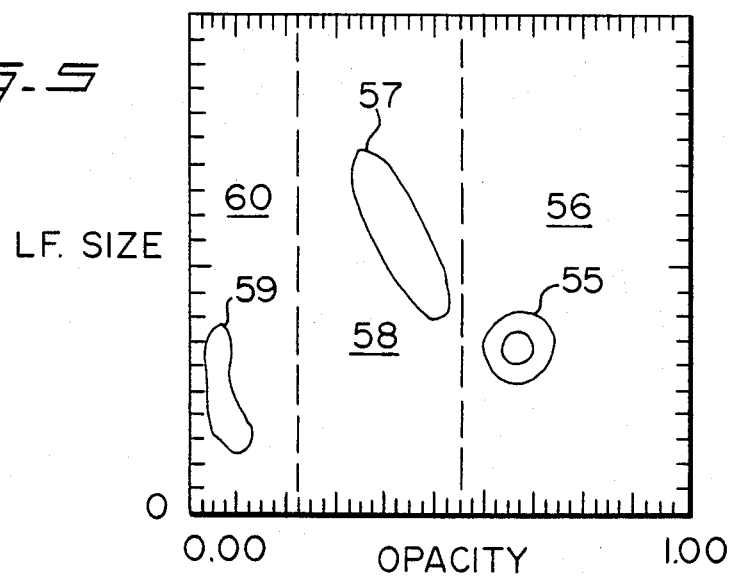
FIG. 5 shows a plotting of particle data points in a system in which the level of osmotic activity is sufficient to create a third subpopulation, ghost cells.

A third example uses the same techniques and apparatus as Example II, except the particle analyzer upon which the method is implemented further includes a well known hydrodynamically focused aperture, such as that shown in FIG. 5 of U.S. Pat. No. 4,014,611 to Simpson, instead of the non-hydrodynamically focused aperture 5 as shown in FIG. 1. More specifically, the apparatus required for Example II is the same as that shown in FIG. 2, when the components in the box 18 are removed, FIG. 2 will be described in more detail hereinafter. In this case, in order to avoid a large amount of signal noise caused by the mixing of a sheath diluent having one conductivity with that of a sample having a different conductivity, the sheath solution is made up of the same solution as is used in the sample, except without the cells being present. In this example the same information content is available as in the previous example with the exception that the hydrodynamically focused aperture will yield more precise size information.

EXAMPLE IV

Figure 2:
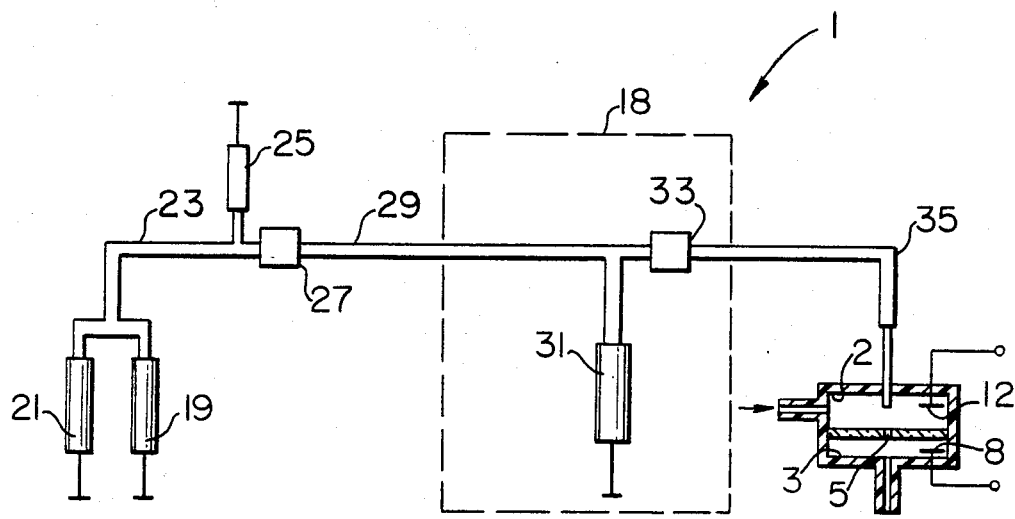
FIG. 2 shows a flow cytometer which is a modification of the one shown in FIG. 1 and is usable with the remaining embodiments.

In the particle analyzer arrangement 1 as set up for Example III and as shown in FIG. 2, there is no electrical incompatibility between the sheath and the sample. In Example IV the procedure is the same, except the sample is mixed with a sheath of physiological saline just before the aperture, such that very little time is allowed for the cells to sense this change in osmolality. Then a measurement of the cells in their fully stressed state can be made without having to adjust the sheath diluent and while using a hydrodynamically focused aperture. In other words, contrary to Example III, in Example IV there is no electrical incompatibility between the sheath and the sample. The same information content is available as in Example III.

EXAMPLE V

In Example V, a procedure and particle analyzing apparatus 1 are used for returning the sample to a normal physiological saline after the osmotic shock. If enough time is allowed between this process and that of monitoring the cells in the signals, the cells will be able to return to their normal size so that the increased size information under osmotic stress is lost. This can be accomplished by exposing the cells to normal physiological saline for a sufficient time to return the cells to their original sizes. Even though the above-described size information is lost, it will be possible to use either the opacity signal or the HF size signal to distinguish between the ghost cells and the unaltered intact cells. Thus, for example, the osmolality at which 50% lysis occurs and the rate of lysis can be measured. The LF size will need to be used to monitor the ghost cells as their opacity or HF signal becomes very small and may become undetectable.

FIG. 2 illustrates an apparatus which can be used with the procedure of Example V. In this particle analyzer 1, a first syringe 19 provides physiological normal saline, i.e., isotonic diluent, and a second syringe 21 provides a solution capable of varying the osmolality of the saline solution from the first syringe 19. Hence, a hypotonic saline solution is provided through conduit 23 and is mixed with the blood sample provided from a third syringe 25. The blood sample and the hypotonic solution are mixed in a mixing junction 27 and fed to a conduit 29 having a length which determines the time of immersion of each blood cell in the hypotonic suspension solution. A fourth syringe 31 provides physiologically normal saline which mixes with the hypotonically suspended blood sample in a second mixing junction 33 such that the sample solution approaches isotonic saline. The solution from the mixing junction 33 is fed into a delay conduit 35, the length of which will determine the amount that the cells will return to their original size. The particle suspension is fed from the delay conduit 35 to a flow cell 37. The flow cell 37 has the first vessel 2 and the second vessel 3 with a dividing wall, having the aperture 5, separating the two vessels. The electrode 12 is in the first vessel and the electrode 8 is in the second vessel. This flow cell arrangement is the same as shown in FIG. 1, except a sheath liquid comprising normal physiological saline is introduced through the inlet 39. In a well known manner, this sheath liquid is used to hydrodynamically focus the cells as they pass through the aperture 5. This distinguishes this system from the non-hydrodynamically focused aperture of FIG. 1. The particle analyzer 1 of FIG. 2 provides sufficient apparatus for accomplishing Example V, as previously explained. If the components of the mixing junction 33 and the syringe 31, which are shown within the box 18, are removed and the conduit 29 is connected directly to the conduit 35, then there exists an apparatus capable of practicing the procedures of Examples III and IV. In Example III, the inlet 39 would be fluidly connected to the conduit 23 so that the sample and sheath will have essentially the same osmolality. In Example IV, the sheath liquid is provided by an independent source and comprises a normal physiological saline. In both examples, the time of exposure of the cells to the hypotonic volume changing solution will be primarily a function of the combined length of the conduits 29 and 35. If the hydrodynamically focusing sheath, which enters the inlet 39, is eliminated in the apparatus of FIG. 2, and a non-hydrodynamically focused aperture 5 is used, such as shown in FIG. 1, then a particle analyzing apparatus is provided in which the procedures of Example II can be implemented. Moreover, with the removal of the components from box 18 and the sheath flow through inlet 39, the apparatus becomes that which is described in incorporated U.S. Pat. No. 4,278,936; hence, this apparatus will not be described in detail herein. Although automated apparatuses have been described for implementing the method of embodying the invention, various manual and semiautomatic apparatus arrangements can be used to practice the invention, a few such arrangements being described in incorporated U.S. Pat. No. 4,278,936.

RESULTS

The following table gives the test results, using the procedures of Example V, of a blood sample from a normal individual and a blood sample from an individual having Beta-thalassemia.

| Sample | Osmolality | % Unaltered | % Altered |
|---|---|---|---|
| Normal | *330 | 100 | 0 |
|  | 165 | 98 | 2 |
|  | 132 | 67 | 33 |
|  | *109 | 9 | 91 |
|  | 83 | 0 | 100 |
| Beta- | *330 | 100 | 0 |

-continued

| Sample | Osmolality | % Unaltered | % Altered |
|---|---|---|---|
| thalassemia | 165 | 91 | 9 |
| | 132 | 74 | 26 |
| | *109 | 31 | 69 |
| | 83 | 0 | 100 |

Figure 3A:
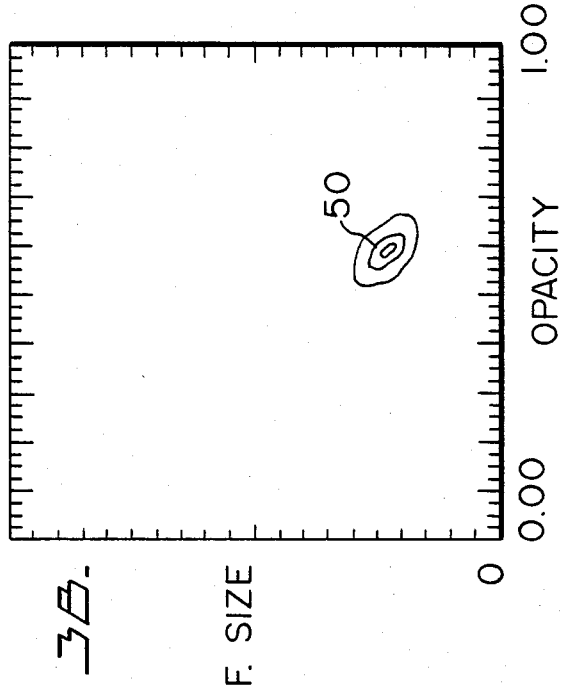
Figure 3B:
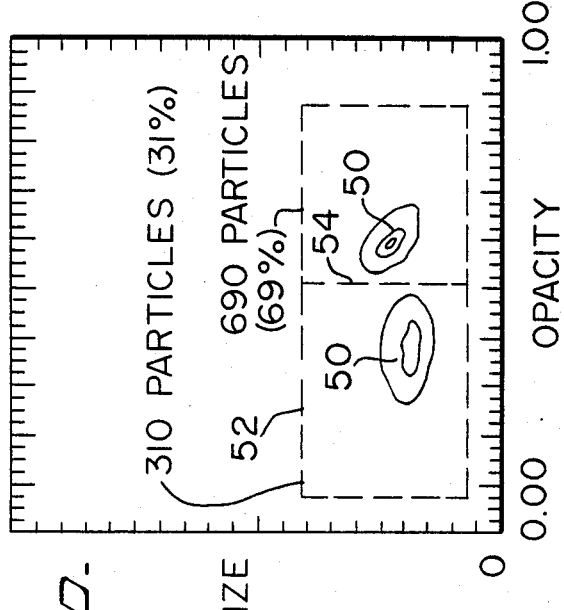
Figure 3C:
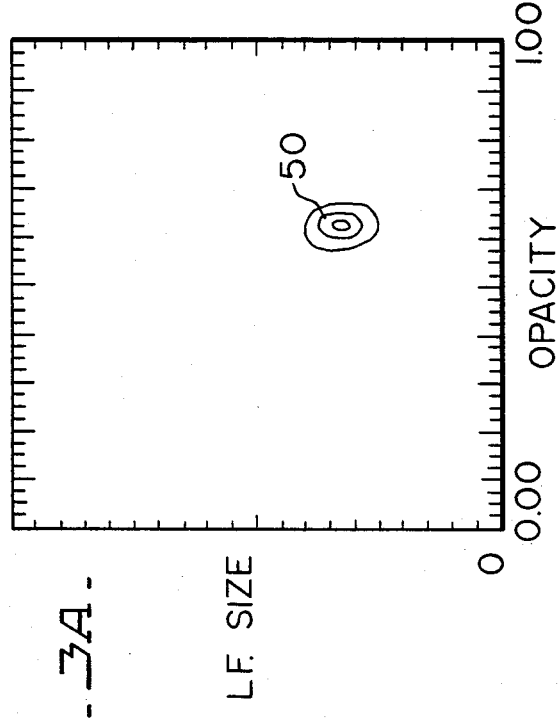
Figure 3D:
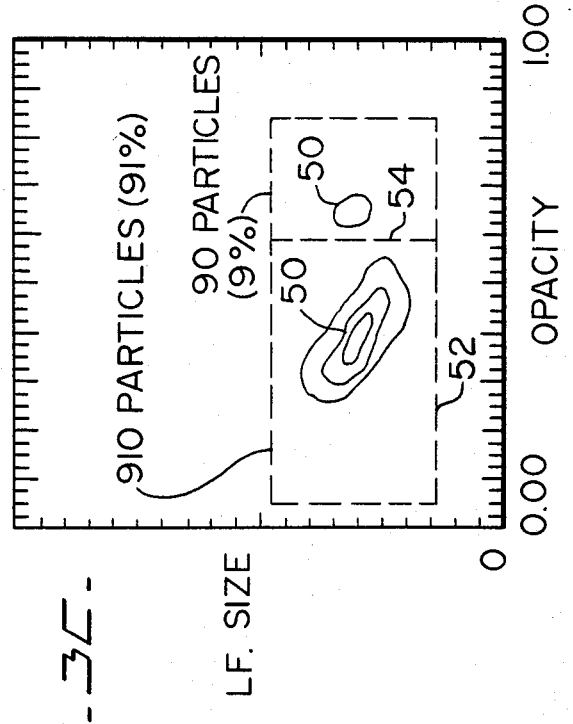

As can be seen from the above data, the Beta-thalassemia blood cells on average are more resistant to an osmotic shock; hence, they have lower percentages of altered cells and therefore higher percentages of unaltered cells, when compared to a normal blood sample. The data for a few of the osmolality levels, which have asterisks above, are shown in FIGS. 3A, 3B, 3C and 3D. From these plots it can be seen how the data for each cell is used to catagorize the cells into the two subpopulations of unaltered or altered cells. Each of the plots have, on the abscissa axis, opacity and have, on the ordinate axis, LF size. The LF size and opacity signals are correlated for each cell so as to define a single point on a given LF size-opacity plot. However, instead of showing many thousands of points which would exist from a single processed sample, the positioning and number of points are illustrated by contour lines 50, which approximately illustrate the location of clusters of cells and their number. FIGS. 3A and 3B illustrate the cell clusters for a normal blood sample and a Beta-thalassemia sample, respectively, at a normal osmolality of 330 milliosmols. FIGS. 3C and 3D illustrate the cell clusters for the normal blood sample and the Beta-thalassemia sample, respectively, in a hypotonic saline solution having an osmolality of 109 milliosmols. Dashed lines 52 are used to illustrate the data boundaries which enclose the data representing altered and unaltered cells. A dividing line 54 separates the two subpopulations. As shown by the above graph and the plots of FIGS. 3C and 3D, at 109 milliosmols, there are significantly more cells classified as unaltered than as altered with Beta-thalassemia as compared to normal blood.

Figure 4:
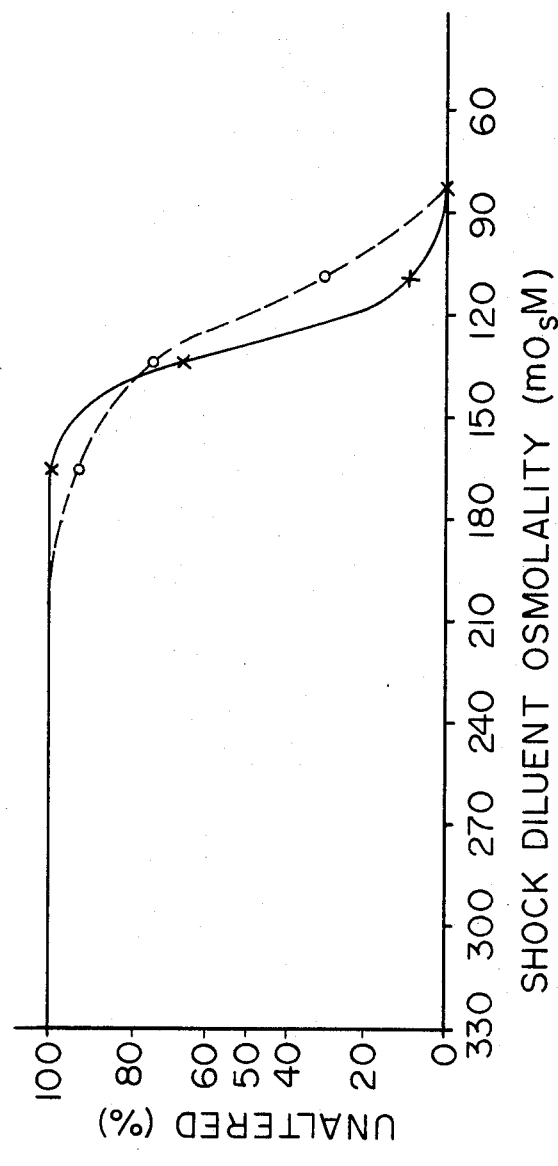
FIG. 4 shows two curves, which represents the plotting of the percent of the cells that were unaltered for the normal and abnormal blood sample shown in FIGS. 3A through 3D.

With the use of standard statistics, preferably implemented with a computer and plotting means, the data in the above graph can be plotted, with, for example, the abscissa being osmolality and the ordinate being numbers of unaltered cells, or, alternatively, altered cells, as shown in FIG. 4. In FIG. 4 the data of the above graph is plotted with the normal blood being shown with a solid line and the Beta-thalassemia line being shown with a dashed line. The curves for different blood samples can be easily quantified to allow for differences between curves to be obtained readily. For instance, from the curves of FIG. 4, the following statistical indices can be ascertained:

| | Normal Blood | Beta-thalassemia |
|---|---|---|
| Midpoint (mOsM) | 127.5 | 118.5 |
| Slope (% change in altered cells per mOsM) | 0.31 | 0.56 |

As can be seen from midpoint and/or slope indices, this data provides the means for quantitatively determining the differences between normal and abnormal bloods.

In the above data, the osmotic activity did not reach levels to create the third population of ghost cells. This was due to the exposure of the cells, as determined by the length of the conduit 29, being only a few seconds. On the other hand, FIG. 5 shows the development of all three subpopulations. This data was obtained by using the procedures of Example I. The osmolality of the liquid was 310 mOsM and the time of immersion in the saponin solution was 170 seconds. The unaltered cells are shown by contour lines 55 and are contained within a box 56, the altered cells are shown by contour line 57 and are contained within a box 58, and the ghost cells are shown by contour line 59 and are contained within a box 60. With the data of FIG. 5, the measurement of opacity is sufficient to create the boxes 56, 58 and 60, except the LF signal is needed to detect the presence of ghost cells that provide a neglible or non-detectable opacity signal.

Although particular embodiments of the invention have been shown and described herein, there is no intention to thereby limit the invention to the details of such embodiments. On the contrary, the intention is to cover all modifications, alternatives, embodiments, usages and equivalents of the subject invention as fall within the spirit and scope of the invention, specfication and the appended claims.

What is climed is:

1. In a method wherein osmotic activity of biological cells is induced by an osmotic or lytic shock and is monitored in a particle analyzer having an aperture for electronic particle volume sensing, the improvement comprising the steps of:
    passing a high frequency current through said aperture to generate a detectable high frequency signal for each cell passing therethrough;
    detecting said high frequency signals;
    classifying the cells into subpopulations, representative of the state of osmotic activity of each cell, by their said high frequency signals.

2. The method according to claim 1, wherein said step of classifying the cells comprises separating said high frequency signals which exceed a given threshold value into a population representative of unaltered cells and which are below said threshold value into a population representative of altered cells.

3. The method according to claim 2, wherein said unaltered cells have said high frequency signals which remain essentially constant during the osmotic activity and wherein said altered cells have said high frequency signals which become lower during the osmotic activity.

4. The method according to claim 1, further comprising,
    passing a low frequency current through said aperture to generate a detectable low frequency signal for each cell passing therethrough;
    correlating said low frequency and said high frequency signals on a cell by cell basis;
    dividing said high frequency signal by said low frequency signal for each cell to obtain an opacity signal;
    said step of classifying the cells into subpopulations comprises classifying the cells by their detected said opacity signals.

5. The method according to claim 4, wherein said step of classifying the cells comprises separating said opacity signals which exceed a given threshold value into a population representative of unaltered cells and which are below said threshold valve into a population representative of altered cells.

6. The method according to claim 4, wherein said unaltered cells have said opacity signals which remain essentially constant during the osmotic activity and wherein said altered cells have said opacity signals which become lower during the osmotic activity.

7. In the method according to claim 1, further comprising,
  passing a low frequency current through said aperture to generate a detectable low frequency signal for each cell passing therethrough;
  detecting said low frequency signal;
  correlating the low frequency and the high frequency signals on a cell by cell basis;
  said step of classifying the cells into subpopulations further including using the detected said low frequency and said high frequency signals in combination.

8. In the method according to claim 7, said biological cells including red blook cells, wherein said step of classifying comprises classifying as a ghost cell each red blood cell that gives a low frequency signal but a very small or negligible high frequency signal.

9. In the method according to claim 7, wherein said step of classifying the cells comprises developing a two dimensional matrix of data points, each said point representing said high frequency signal and said low frequency signal for a given cell and catagorizing cells during said osmotic activity into subpopulations of unaltered cells which display an unaltered low frequency signal, altered cells which have an altered low frequency signal and ghost red blood cells which have a very small or negligible high frequency signal.

10. In the method according to claim 1, further comprising,
  passing a low frequency current through said aperture to generate a detectable low frequency signal for each cell passing therethrough;
  detecting said low frequency signals;
  correlating said low frequency and said high frequency signals on a cell by cell basis;
  dividing said high frequency signal by said low frequency signal for each cell to obtain an opacity signal;
  said step of classifying the cells into subpopulations further including using said low frequency signal and said opacity signal in combination.

11. In the method according to claim 10, said biological cells including red blood cells, wherein said step of classifying comprises classifying as a ghost cell each red blood cell that gives a low frequency signal but a very small or negligible opacity signal.

12. In the method according to claim 10, wherein said step of classifying the cells comprises developing a two dimensional matrix of data points, each said point representing said opacity signal and said low frequency signal for a given cell and catagorizing cells during said osmotic activity into subpopulations of unaltered cells which display an unaltered low frequency signal, altered cells which have an altered low frequency signal and ghost red blood cells which have a very small or negligible high frequency signal.

13. The method according to any one of the claims 1, 4, 7, and 10, wherein said osmotic activity comprises setting the hypotonicity of said suspension solution at a given value and said steps of detecting comprise detecting said signals while the cells are immersed in said hypotonic suspension liquid so that said signals become a function of the length of time the cells have been immersed in said hypotonic suspension liquid.

14. The method according to any one of claims 1, 4, 7, and 10, wherein said osmotic activity comprises setting the concentration of a lytic agent in said suspension solution at a given level and said steps of detecting comprise detecting said signals while the cells are immersed in said lytic-containing suspension liquid so that said signals become a function of the length of time the cells have been immersed in said lytic-containing suspension liquid.

15. The method according to any one of claims 1, 4, 7, and 10, wherein said osmotic activity comprises decreasing the osmolality of said suspension solution over a predetermined range of hypotonicity and allowing each cell to be immersed in said suspension solution at a given value of hypotonicity within said range for a constant length of time and said steps of detecting comprise detecting said signals of cells after the cells have been immersed for said constant length of time so that said signals become a function of osmolality.

16. The method according to claim 15, further comprising, after a period of immersing the cells in said suspension liquid of a given hypotonicity, the steps of mixing said suspension liquid with normal physiological saline to return the solution suspending the cells to normal osmolality and said steps of detecting said signals comprise detecting the signals after the solution suspending the cells has returned to normal osmolality but prior to the cells having time to return to their original sizes.

17. The method according to claim 15, further comprising, after a period of immersing the cells in the suspension liquid of a given hypotonicity, the step of mixing said suspension liquid with normal physiological saline to return the solution suspending the cells to normal osmolality and the step of detecting said signals comprise detecting said signals after the solution suspending the cells has returned to normal osmolality and the cells have had sufficient time to return to their original sizes.

18. The method according to any one of the claims 1, 4, 7, and 10, wherein said osmotic activity comprises increasing the concentration of a lytic agent in said suspension solution over a predetermined range of concentration and allowing each cell to be immersed in said lytic agent-containing suspension solution at a given concentration of said lytic agent within said range for a constant length of time and said steps of detecting comprising detecting said signals of cells after the cells have been immersed for said constant length of time so that said signals become a function of the concentration of said lytic agent.

19. In a method for monitoring biological cells in a particle analyzer having an aperture for electronic sensing of particles on a cell by cell basis, the improvements comprising the steps of:
  inducing osmotic activity in at least some of the cells by osmotic shock thereto;
  passing a high frequency current through said aperture to generate a detectable high frequency signal for each cell passing therethrough;
  detecting said high frequency signals;
  classifying the cells into subpopulations, representative of the state of osmotic activity of each cell, by their said high frequency signals.

* * * * *